United States Patent
Zhang et al.

(10) Patent No.: US 9,835,558 B2
(45) Date of Patent: Dec. 5, 2017

(54) AGGREGATION-INDUCED EMISSION LUMINOGEN HAVING AN PEPTIDE SEQUENCE AND ITS USES THEREOF

(71) Applicants: Chunqiu Zhang, Beijing (CN); Guozhang Zou, Bloomington, IN (US)

(72) Inventors: Chunqiu Zhang, Beijing (CN); Guozhang Zou, Bloomington, IN (US)

( * ) Notice: Subject to any disclaimer, the term of this patent is extended or adjusted under 35 U.S.C. 154(b) by 0 days.

(21) Appl. No.: 14/721,791

(22) Filed: May 26, 2015

(65) Prior Publication Data

US 2016/0349245 A1    Dec. 1, 2016

(51) Int. Cl.
*C07K 14/00* (2006.01)
*G01N 21/64* (2006.01)
*G01N 33/58* (2006.01)
*G01N 33/92* (2006.01)
*C12N 15/64* (2006.01)

(52) U.S. Cl.
CPC ......... *G01N 21/6428* (2013.01); *C12N 15/64* (2013.01); *G01N 33/582* (2013.01); *G01N 33/92* (2013.01)

(58) Field of Classification Search
None
See application file for complete search history.

(56) References Cited

U.S. PATENT DOCUMENTS

2004/0242854 A1* 12/2004 Osborn .............. A61K 49/0002
530/409
2013/0216593 A1* 8/2013 Borden .............. A61K 41/0028
424/400

* cited by examiner

*Primary Examiner* — Jeanette Lieb
(74) *Attorney, Agent, or Firm* — Jie Tan; JT Law Services, PC

(57) ABSTRACT

A fluorescence molecular probe having a hydrophilic polypeptide backbone conjugated with a hydrophobic alkyl chain and a function group with aggregation induced emission is disclosed. The hydrophilic peptide sequence renders DNA binding capacity and the hydrophobic alkyl chain provides capacity for embedding within cell membrane. The aggregation induced emission renders real time tracking for live cell function studies. The synthesis of the probe is simple and easy for purification.

10 Claims, 17 Drawing Sheets

AGGREGATION-INDUCED EMISSION LUMINOGEN HAVING AN PEPTIDE SEQUENCE AND ITS USES THEREOF

CROSS-REFERENCE

Priority is claimed from the China Patent Application No. 201410231022.9, filed on May 28, 2014, as well as the U.S. Provisional Patent Application 62/150,275 filed on Apr. 20, 2015. The entirety of these previous filings is hereby incorporated by reference.

TECHNOLOGY FIELD

The present application relates to a luminogen compound molecule capable of aggregation-induced emission (AIE), and more particularly to a novel luminogen compound molecule that has a peptide sequence consisting of charged amino acid residues as hydrophilic moiety to target lipid membranes and DNA and a palmiticacid (PA) and tetraphenylethylene (TPE) side chains to provide a lipophilic moiety for lipid membrane insertion where the TPE moiety can "turn on" luminescence upon being embedded in a lipid membrane. This novel luminogen is superiorly suitable for being used in real-time cell membrane tracking due to its none or low toxicity to live cells and high photo-stability. Its ability to bind DNA renders it an ideal dye for visualizing the DNA transfection process in Bio-engineering and any other Molecule Biology endeavors.

DESCRIPTION OF RELATED ART

Note that the points discussed below may reflect the hindsight gained from the disclosed inventions, and are not necessarily admitted to be prior art.

The cytoplasmic membrane is the two-dimensional boundary between a living cell and its environment. Cytoplasmic membrane-related events, including dynamic membrane remodeling, signal transduction, and nutrient transport, are of great interest to cell biologists. To study these events, it is very important to develop probes for subcellular fluorescence imaging that can identify the cytoplasmic membrane and record the dynamic changes.

Organic molecules and functional groups of fluorescence have been used for probe development. Traditional fluorescent dyes such as fluorescein isothiocyanate (FITC), rhodamine, propidium iodide, ethidium bromide, Nile Red, BODIPY dyes, etc. have been used for various cell staining and imaging. However, these traditional dyes have the problem to show very low fluorescence in aggregated state or can be easily photo bleached during imaging process. Furthermore, tracking cell membranes requires fluorescent-labeled probe molecules to target and bind onto cell membranes, which generally causes aggregation effect to the fluorescent molecules. Aggregation-caused quenching has thus seriously obstructed the advancement of studies of cell membrane tracking.

Accordingly, there are only few commercial fluorescent dyes available for tracking cell membranes, such as DiO and DiI. Typically, these probes have a lipophilic structure that allows them to become embedded into cell membranes; however, they generate background fluorescence even when they are not binding to cell membranes, resulting in a low signal-to-noise (S/N) ratio. In addition, they also are susceptible to photo bleaching under laser exposure, which means they are not suitable for long-term observation or real-time tracking.

Fluorescently labeled proteins, such as labeled lectins that bind to cell surface sugars, are an alternative type of membrane probe. However, these probes result in inconsistent staining with variations across cell types. Therefore, it is desirable to develop new photostable fluorescent probes that specifically and consistently stain the cell membrane with low other background staining.

The development of bioprobes that can be fluorescently "turned on" by aggregation is thus of great importance to the study of cell membrane tracking Recently, the unique property of aggregation-induced emission (AIE) of several luminogens have been discovered. These luminogens include tartrazine groups and tetraphenylethylene (TPE) groups. Their AIE mechanism may be due to the restriction of intermolecular rotation (RIR), which prohibits energy dissipation and leads to high quantum yield. Because of the RIR effect, TPE-based AIE luminogens may become highly fluorescent when individually dispersed molecules are entrapped in a tight space, even though no aggregation happens. In contrast to conventional fluorescent dyes, TPE-based AIE luminogens exhibit bright emission in the aggregated state when intramolecular motion is hindered, but no or very weak emission in the monodisperse state when intramolecular motion is unrestricted.

A number of AIE-based bioprobes have been developed to track specific organelles in the cell or for selectively monitoring real time biological processes with different TPE derivatives or AIE structures. For example, AIE-Lyso-1 chemical was shown to specifically target and monitor lysosomes (Gao, M., et al., "A Fluorescent Light-up Probe with 'AIE+ESIPT' Characteristics for Specific Detection of Lysosomal Esterase. J. Mater. Chem. B, 2014, 2, 3438-3442, the entirety of which is hereby incorporated by reference). TPE-AmA1 has been shown to specifically stain lipid droplets (LDs) inside a cell (Wang, E., et al., "A Highly Selective AIE Fluorogen for Lipid Droplet Imaging in Live Cells and Green Algae." J. Mater. Chem. B, 2014, 2, 2013-2019, the entirety of which is hereby incorporated by reference.) TPE-TPP has been shown to stain Mitochondria (Leung, C. W., et al., "A Photostable AIE Luminogen for Specific Mitochondrial Imaging and Tracking" J. Am. Chem. Soc. 2013, 135, 62-65, the entirety of which is hereby incorporated by reference). TPE-Q19, a TPE having a conjugated peptide sequence, has been shown to form luminescent hydrogel under certain salt conditions (Zhang, C., et al., "Salt-Responsive Self-Assembly of Luminescent Hydrogel with Intrinsic Gelation-Enhanced Emission." ACS Appl. Mater. Interfaces. 2014, 6, 757-762, the entirety of which is hereby incorporated by reference).

In addition, the AIE fluorogens are nontoxic to live cells and do not interfere with cell physiology and proliferation. Therefore, there is great need for more AIE-based luminogens that can track specific cell functions.

SUMMARY

The present application discloses a novel AIE bioprobe is capable of cell membrane tracking as well as visualizing DNA transfection process.

In one aspect of the embodiment, this AIE fluorogen probe has a hydrophilic polypeptide backbone conjugated with a hydrophobic alkyl chain and a function group with aggregation induced emission. The hydrophobic alkyl chain may contain 8-20 carbon length.

In one aspect of the embodiment the hydrophilic polypeptide is a short sequence of positively charged peptide sequence that is covalently conjugated to a tetraphenylethylene or tetraphenylsilole as hydrophilic moiety to target cell membranes as well as DNA; in addition, a lipid acid side chain is covalently conjugated to the peptide through a linker molecule provide a lipophilic moiety for good cell membrane insertion.

In one aspect of the embodiment, the positively charged amino acid sequence is a tetra-peptide sequence consisting of four arginine residues that is conjugated to carboxylated TPE through forming an amide bond with a linker molecule and a palmitic acid (PA), oleic acid or stearic acid is also covalently conjugated to the same linker molecule by forming another amide bond.

In one aspect of the embodiment, (1-[Bis(dimethylamino) methylene]-1H-1,2,3-triazolo[4,5-b]pyridinium 3-oxid hexafluorophosphate) and N,N-Diisopropylethylamine are catalysts to conjugate carboxylated hydrophobic alkyl chain and AIE group to the amino groups of hydrophilic peptide via amide bonds.

In one embodiment, the AIE fluorogen probe is incubated with a liposome to fluorescently label the lipid membrane.

In one embodiment, the AIE fluorogen probe is incubated with a live cell to fluorescently label the cell membrane and visualizing the live cell in real time under fluorescent microscope.

In one embodiment, the AIE fluorogen probe is incubated with a DNA fragment to fluorescently label the DNA fragment, visualizing the DNA fragment in real time during any subsequent process under fluorescent microscope.

In one embodiment, a simple and low cost TPE based AIE-fluorogen probe synthesis method includes synthesis of a peptide and the conjugation of TPE and other functional groups via lysine amino acid as a linker molecule.

The disclosed innovation, in various embodiments, provides one or more of at least the following advantages. However, not all of these advantages result from every one of the innovations disclosed, and this list of advantages does not limit the various claimed inventions. This unique fluorescence probe is capable of labeling live cell membrane and DNA fragment, can thus be implemented for any biomedical research and biotechnology research. The synthesis of the probe is simple and of low cost, does not involve complicated steps or strict conditions, and has good photo-stability for real time tracking application.

BRIEF DESCRIPTION OF THE DRAWINGS

The disclosed application will be described with reference to the accompanying drawings, which show important sample embodiments of the invention and which are incorporated in the specification hereof by reference, wherein.

DETAILED DESCRIPTION OF SAMPLE EMBODIMENTS

Figure 1:
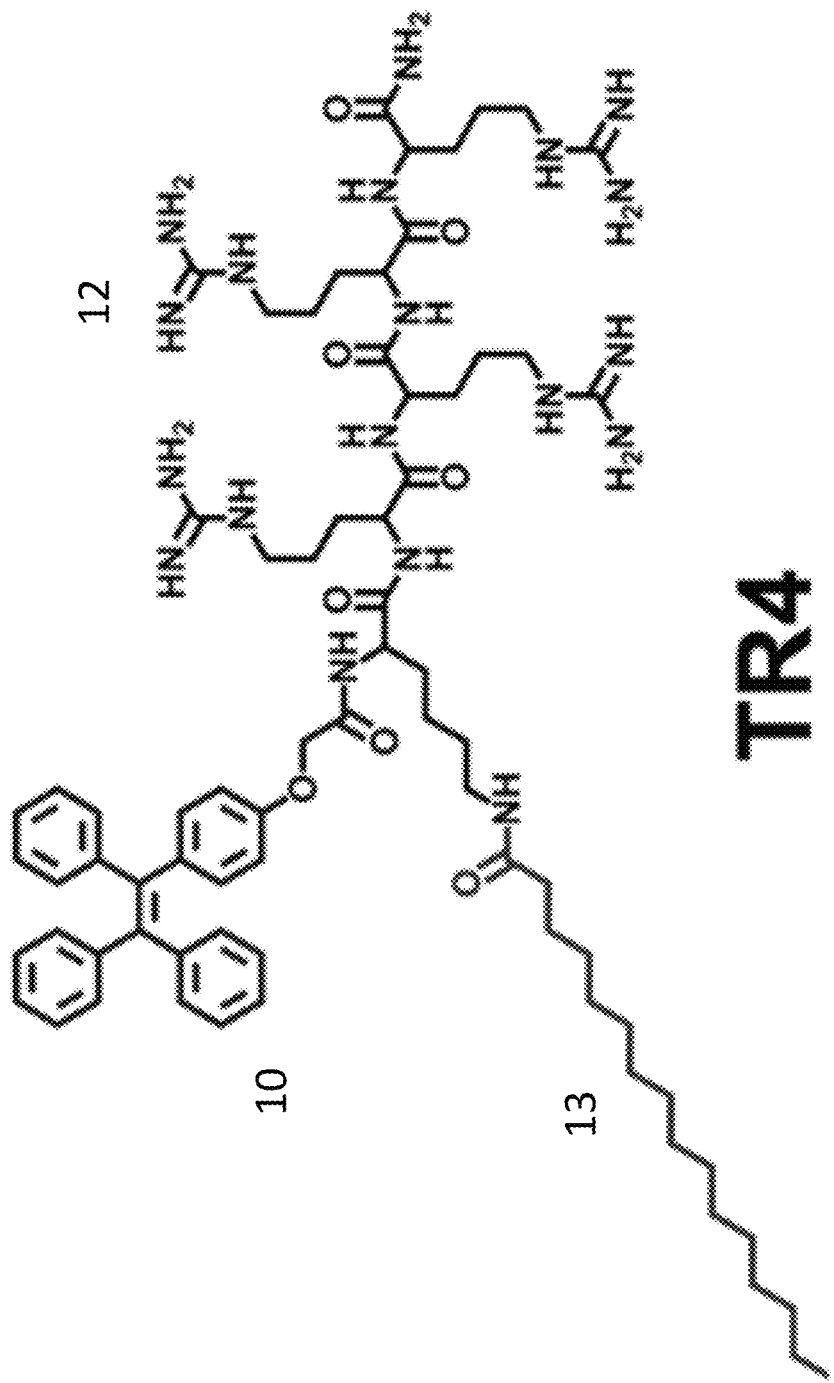
FIG. 1 shows an example AIE fluorogen probe (TR4) that interacts with cell membrane as well as DNA and "turns on" fluorescence emission after the interaction in accordance with this application.

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

The term "a" or "an" as used herein includes the singular and the plural, unless specifically stated otherwise. Therefore, the term "a," "an," or "at least one" can be used interchangeably in this application.

The term "$\lambda_{ex}$" as used herein refers to excitation wavelength in stimulating fluorescence in imaging or spectrum measurement.

The phrase "aggregation" as used herein refers to aggregated state where the interactions between two similar molecules hinders and limits their intermolecular motion, or the state when individually dispersed molecules are entrapped in a tight space. Aggregation is generally caused by non-covalent interactions.

The phrase "monodisperse state" as used hereon refers to a molecule state when intramolecular motion is unrestricted.

The phrase "aggregation caused quenching" or "ACQ" as used herein refers to the phenomenon wherein the aggregation of fluorogen molecules significantly decreases the fluorescence intensity of the fluorogens. The aggregate formation is said to "quench" light emission of thefluorogens.

The phrase "aggregation induced emission" or "AIE" as used herein refers to the phenomenon manifested by compounds exhibiting enhancement of light-emission in fluorescence upon aggregation or in limited space state whereas they exhibit weak or almost no emission in dilute monodispersed state or solutions or in state of free movement.

The phrase "conjugated" as used herein generally refers to two or more molecules/functional groups form covalent chemical bonds with one another as it is used in chemistry or biochemistry field.

The phrase "binding" as used herein generally refers to two or more molecules/functional groups interact via force of affinity and non-covalent bonds with one another as it is used in chemistry or biochemistry field.

The term "DMF" as used herein refers to dimethylformamide, which is an organic compound with the formula $(CH_3)_2NC(O)H$, a common solvent for chemical reactions. The term "DMSO" as used herein refers to dimethylsulfoxide, which is an organic compound having the formula $(CH_3)_2SO$. It is a common solvent for chemical reactions. The term "EDTA" as used herein refers to ethylenediaminetetraaceticacid, a polyamino carboxylic acid and a colorless, water-soluble solid.

The phrase "emission intensity" as used herein refers to the magnitude of fluorescence/phosphorescence normally obtained from a fluorescence spectrometer or a fluorescence microscopy measurement.

The term "fluorogen" as used herein refers to a chemical compound that manifests luminescence under excitation. In this application, fluorogen and luminogen are used interchangeably.

The term "DNA" as used herein refers to deoxyribonucleic acid. The term "RNA" as used herein refers to ribonucleic acid. The term "nucleic acid" as used herein includes both DNA and RNA or their derivatives, as is generally used in chemistry or biochemistry. "Nucleic acid" and "polynucleic acid" may be used interchangeably.

The term "peptide" as used herein refers to a molecule having amide backbone structure formed between a sequence of amino acids or their derivatives, as is generally used in chemistry or biochemistry. As used herein, peptide and poly-peptide may be used interchangeably.

Materials and methods used in this application include the following: Fmoc-amino acids, O-(7-azabenzotriazole-1-yl)-1,1,3,3-tetramethyluronilum hexafluorophosphate (HATU) and diisopropylethylamine (DIEA) were purchased from BO MAI JIE Technology Co., Ltd (Beijing, China). TPE-COOH was synthesized according published methods. To prepare liposomes, hsPC and cholesterol were purchased from Avanti Polar Lipids, Inc. (Alabaster, Ala.). DiI was purchased from Thermo Fisher Scientific Inc. The human breast cancer cell line MCF-7 was purchased from American Type Culture Collection (ATCC; Manassas, Va.). Cell culture medium and fetal bovine serum were from Wisent Inc. (Multicell, Wisent Inc., St. Bruno, Quebec, Canada). 0.25% Trypsin-EDTA and antibiotic solution (penicillin and streptomycin) were purchased from Invitrogen (Invitrogen, Carlsbad, Calif.). Culture dishes and plates were from Corning (Corning, N.Y., USA). The reaction products were analyzed by MALDI-TOF-MS using a Microflex LRF System spectrometer (Bruker Daltonics) and high performance liquid chromatography (HPLC) (Waters 2796). Transmission electron microscopy (TEM) was performed on a Hitachi HT7700 transmission electron microscope with 120 kV acceleration voltage. CLSM (confocal laser scanning microscope) images were obtained by PerkinElmer Ultra VIEW VoX. Two-photon fluorescence microscopy images of TR4 labeled cells were obtained with spectral confocal (Olympus, FV1000). The human breast cancer cell line MCF-7 and the human hepatocellular carcinoma cell line HepG-2 were maintained in Dulbecco's modified Eagle's medium/high glucose with 10% fetal bovine serum in a humidified atmosphere containing 5% $CO_2$ at 37° C. The human umbilical vein endothelial cell (HUVEC) was maintained in Dulbecco's modified Eagle's medium/low glucose with 10% fetal bovine serum.

In reference to FIG. 1, an example alternative cell membrane tracker, amphipathic TR4, an AIE-based luminogen, is designed and constructed. TR4 molecule has a short tetrapeptide sequence 12 consisting of four arginine residues as the positively charged hydrophilic moiety to target membranes. With lysine as linker molecule 15, carboxylatedtetraphenylethylene (TPE) 10 is conjugated to the amide backbone of peptide 12 while a palmitic acid (PA) 13 is linked to the side chain of lysine to provide a lipophilic moiety for membrane insertion. For TPE with its propeller-like molecular structures of four phenyl rings linked on ethane, the restriction to the intramolecular rotations upon aggregation induces its high fluorescence emission.

With the linking of 8-20 carbon of hydrophobic alkyl chain on the molecule, the probe molecule is capable of inserting into the lipid bilayers of liposomes and embedding TPE tightly into the limited space between the two layers of lipid molecules. (TPE) TPE 10 is thus capable of "turn on" luminescence upon TR4 being embedded in cell membrane. The added 8-20 carbon hydrophobic alkyl chain allows TR4 molecules to specifically bind to liposomes and cell membranes, causing further aggregation effect TR4 molecules to the membrane.

Figure 2:
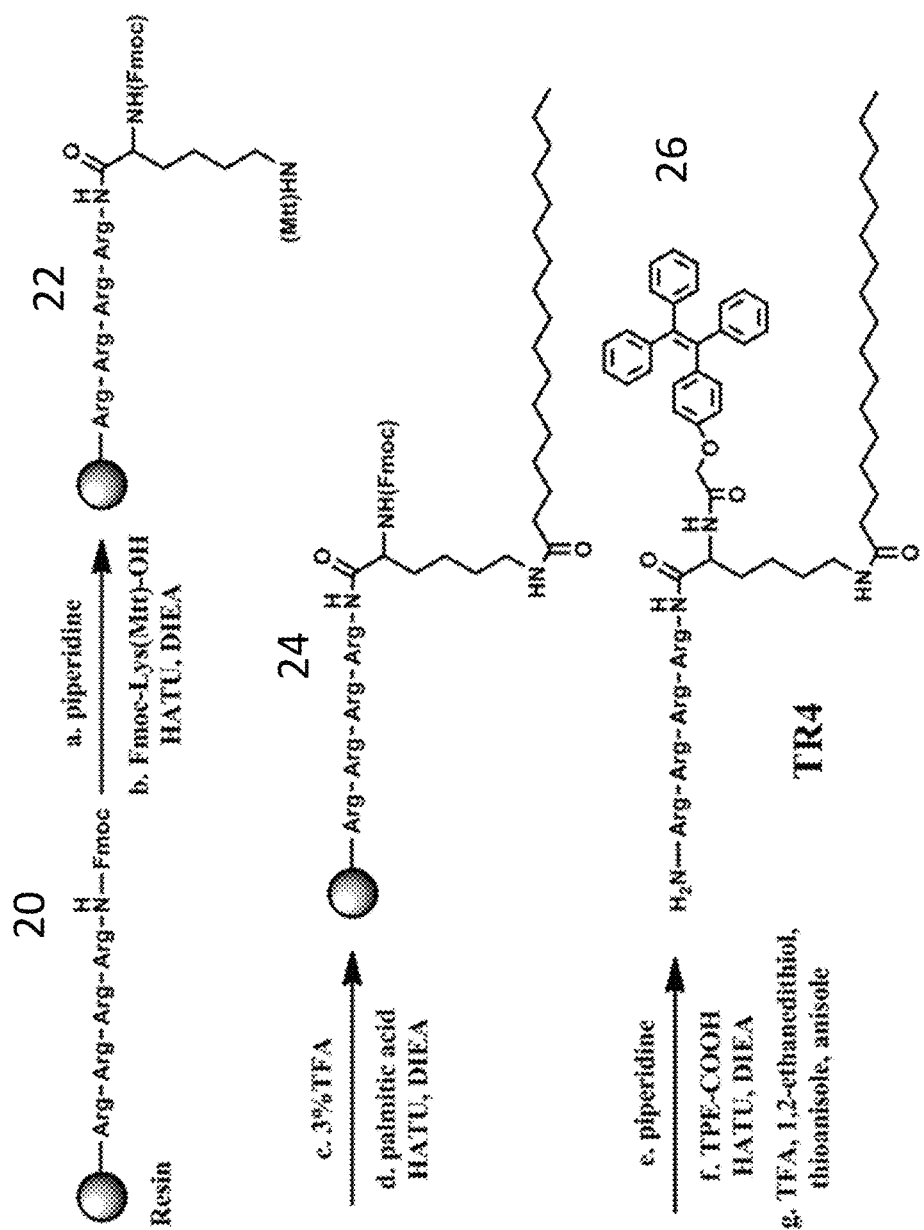
FIG. 2 shows an example chemical synthesis process for the TR4 probe shown in FIG. 1 in accordance with this application.
Figure 3A:
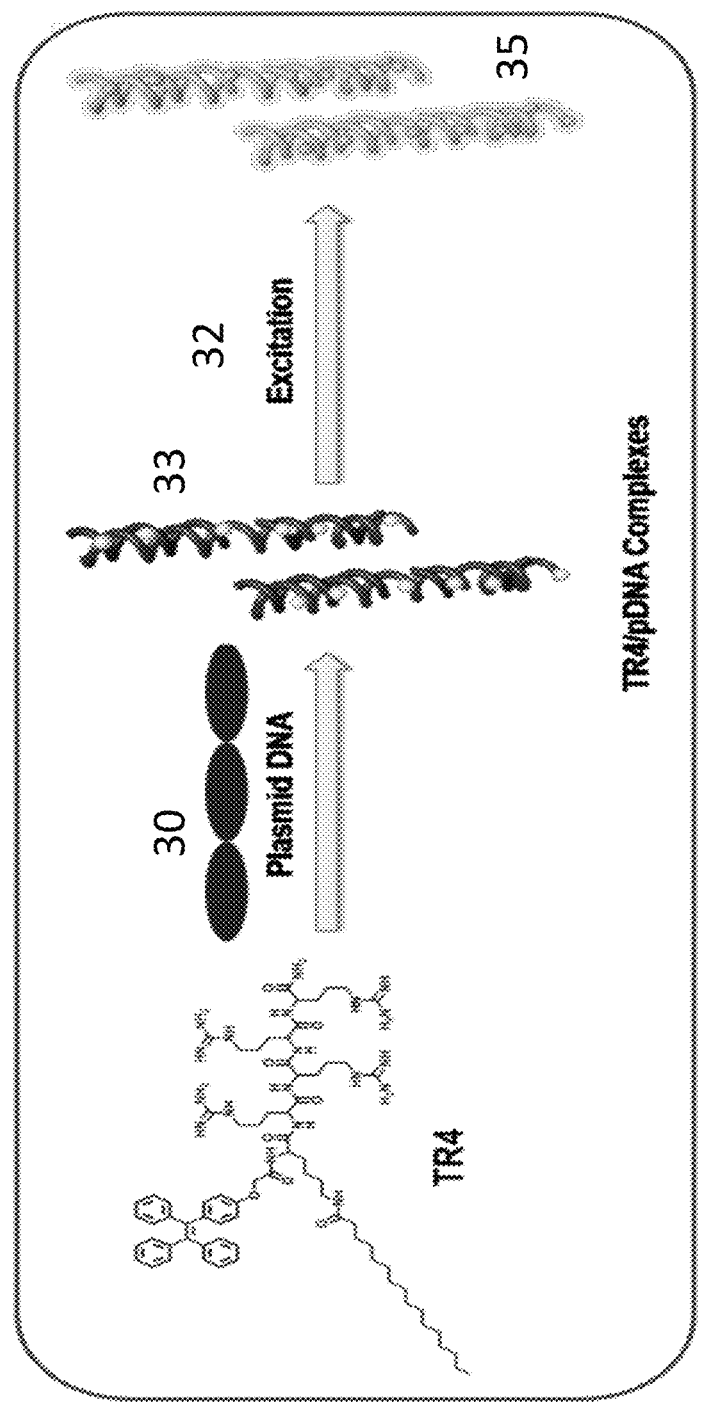
FIG. 3A chemically shows a mechanism of the AIE fluorogen probe in FIG. 1 to bind DNA and "turn on" fluorescence emission after the interaction in accordance with this application.
Figure 3B:
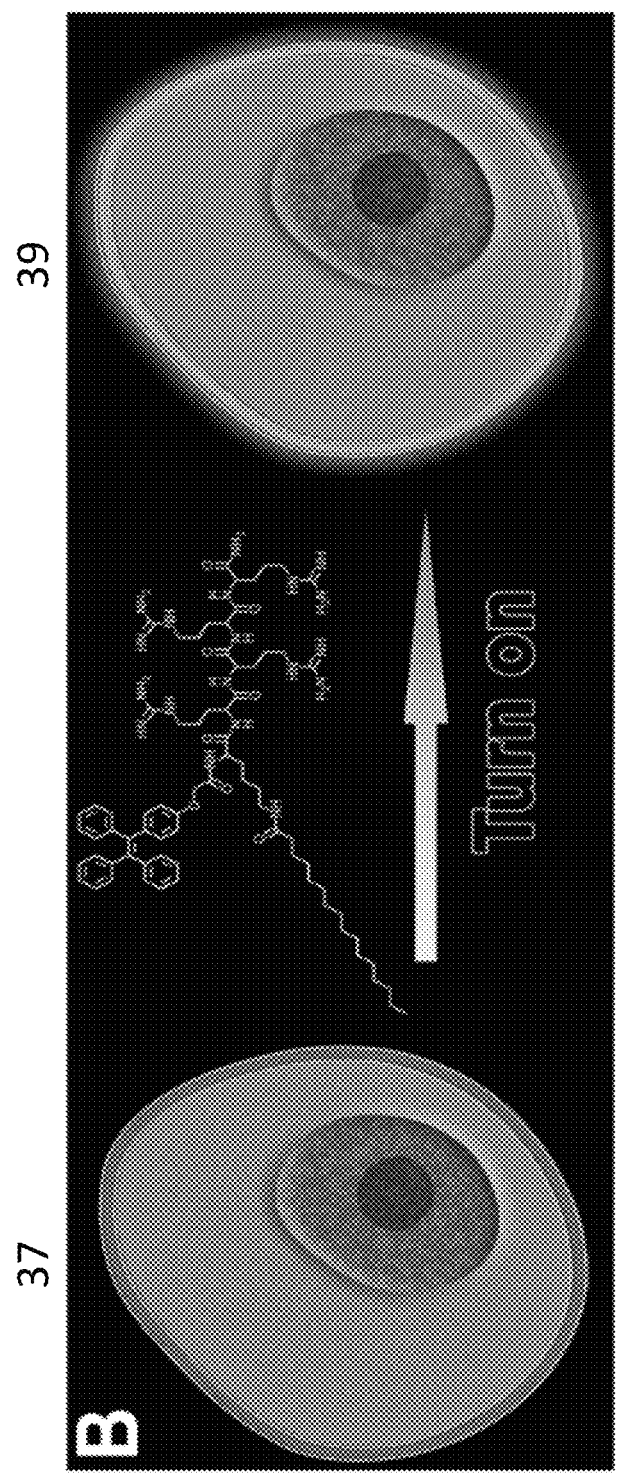
FIG. 3B schematically shows a mechanism of the AIE fluorogen probe in FIG. 1 to insert into cell membrane and "turn on" fluorescence emission after the interaction in accordance with this application.
Figure 4A:
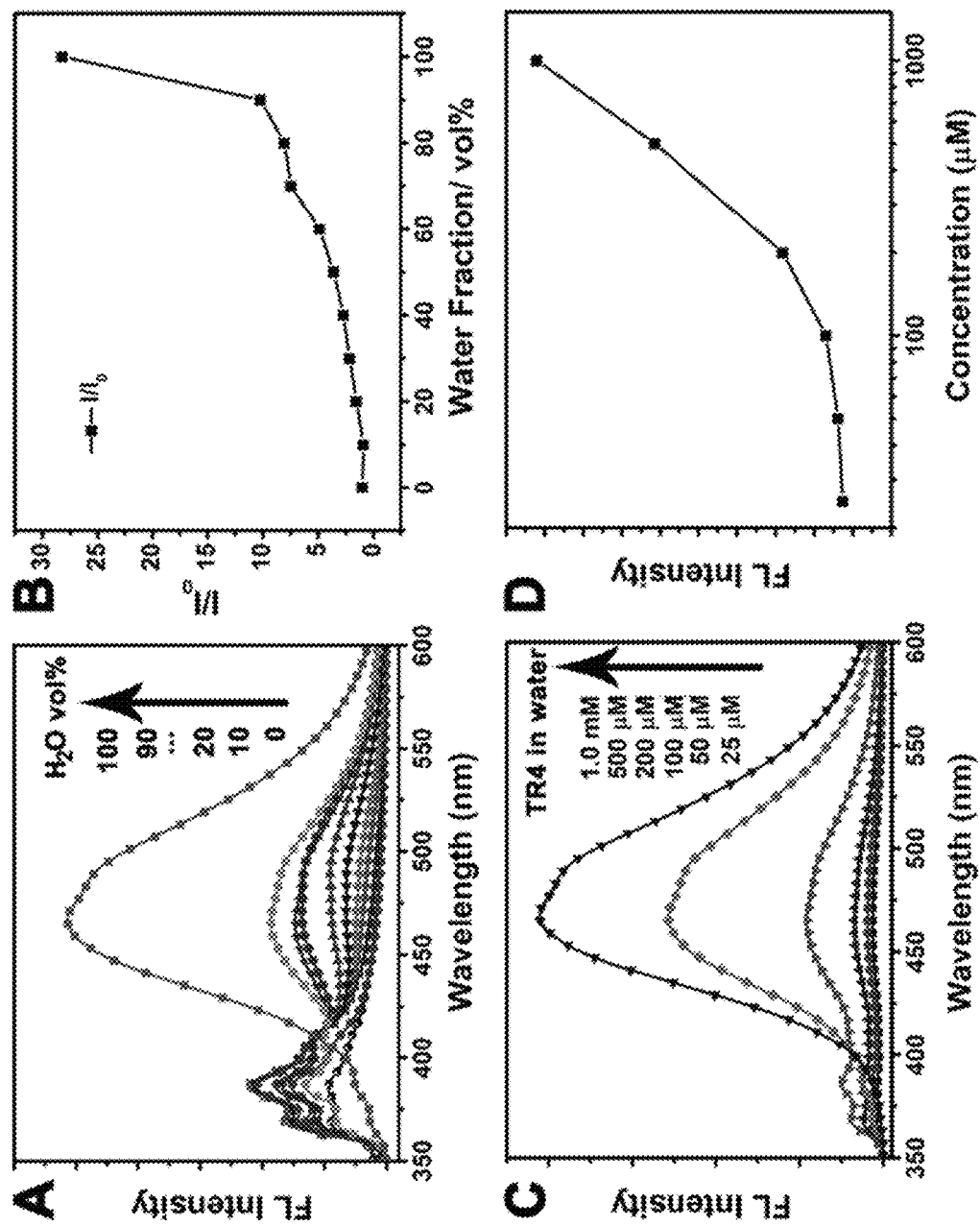
FIG. 4A displays in panel A the fluorescence spectra of TR4 in DMF/water mixtures with different water fractions (vol %) and in panel B the plot off fluorescence intensity (I) of TR4 (500 µM) at 466 nm versus the water fraction of the DMF/water mixture $I_0$=fluorescence intensity of TR4 in pure DMF solution ($\lambda_{ex}$=330 nm). In panel C displays the fluorescence spectra of TR4 at different concentrations (25 µM to 1.0 mM) in water, and panel D the plot of peak fluorescence intensity (466 nm) of TR4 in water versus concentration ($\lambda_{ex}$=330 nm).
Figure 4B:
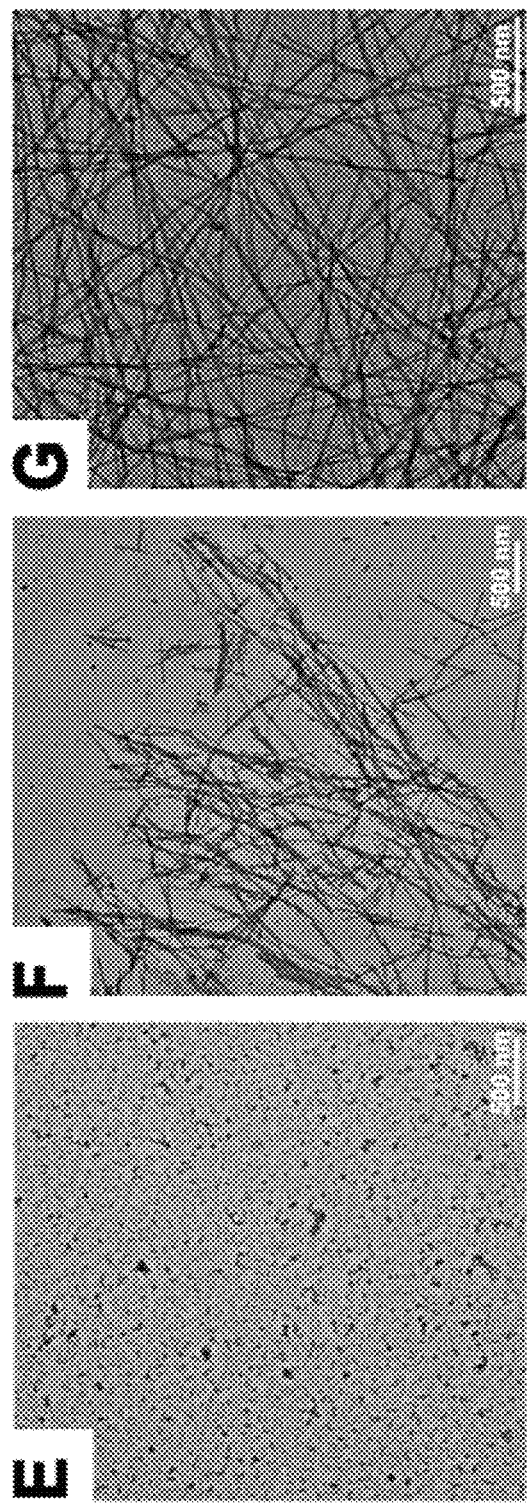
FIG. 4B displays in panel E the TEM image of nanostructures of TR4 at 100 µM, in panel F the TEM image of TR4 at 200 µM, and in panel G the TEM image of TR4 at 500 µM in water.
Figure 5:
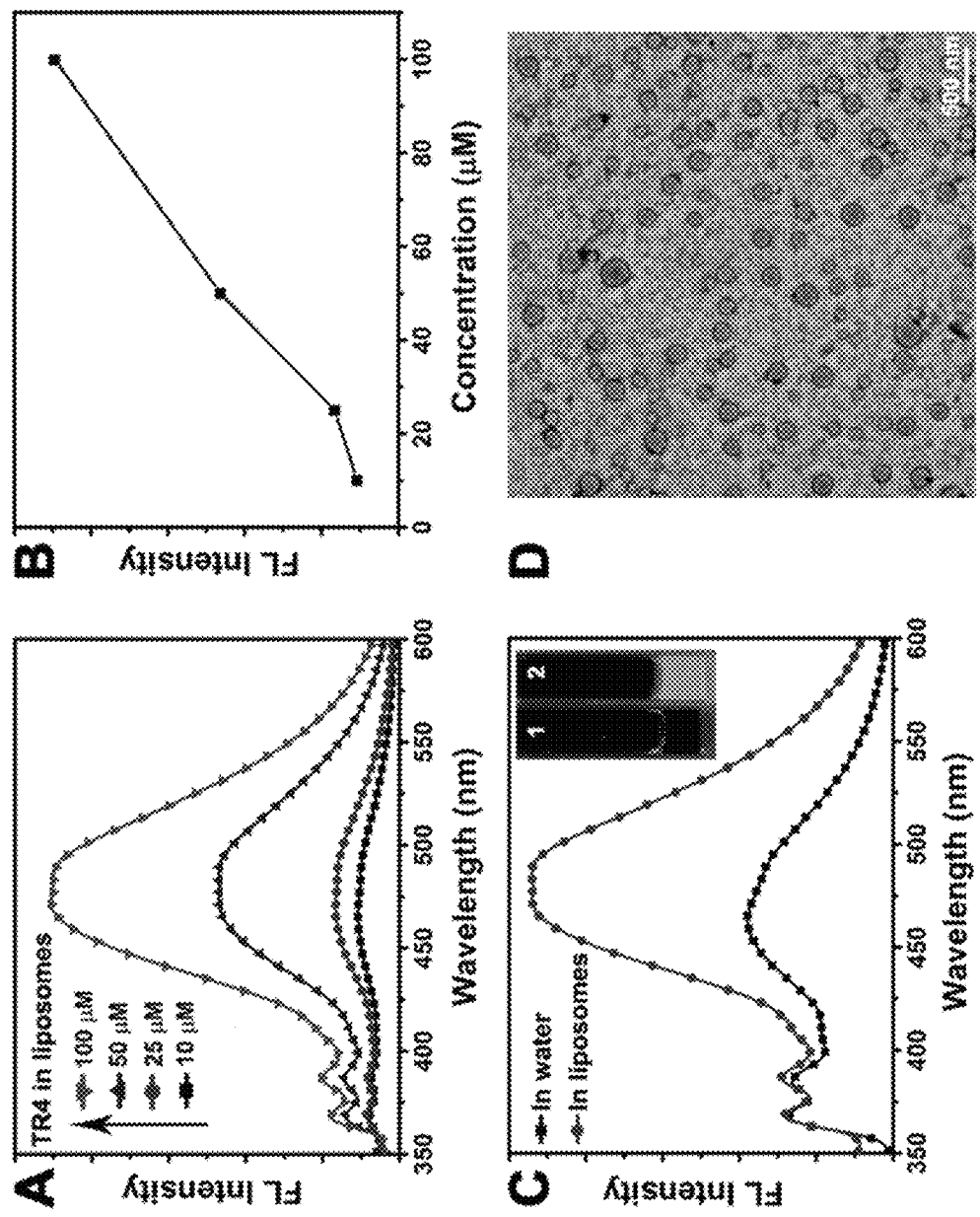
FIG. 5 displays in panel A the fluorescence spectra of TR4 embedding into liposomes, where the concentration of TR4 increases from 10 µM to 100 µM; in panel B the plot of fluorescence intensity of liposomes in the presence of TR4 at 466 nm versus concentration ($\lambda_{ex}$=330 nm); in panel C the fluorescence spectra of TR4 at 50 µM in water or in liposomes wherein the photograph shows fluorescence of TR4 in water (1), and TR4 in liposomes (2) under UV light (365 nm); and in panel D the TEM image of liposomes in the presence of TR4 at 50 µM.
Figure 6:
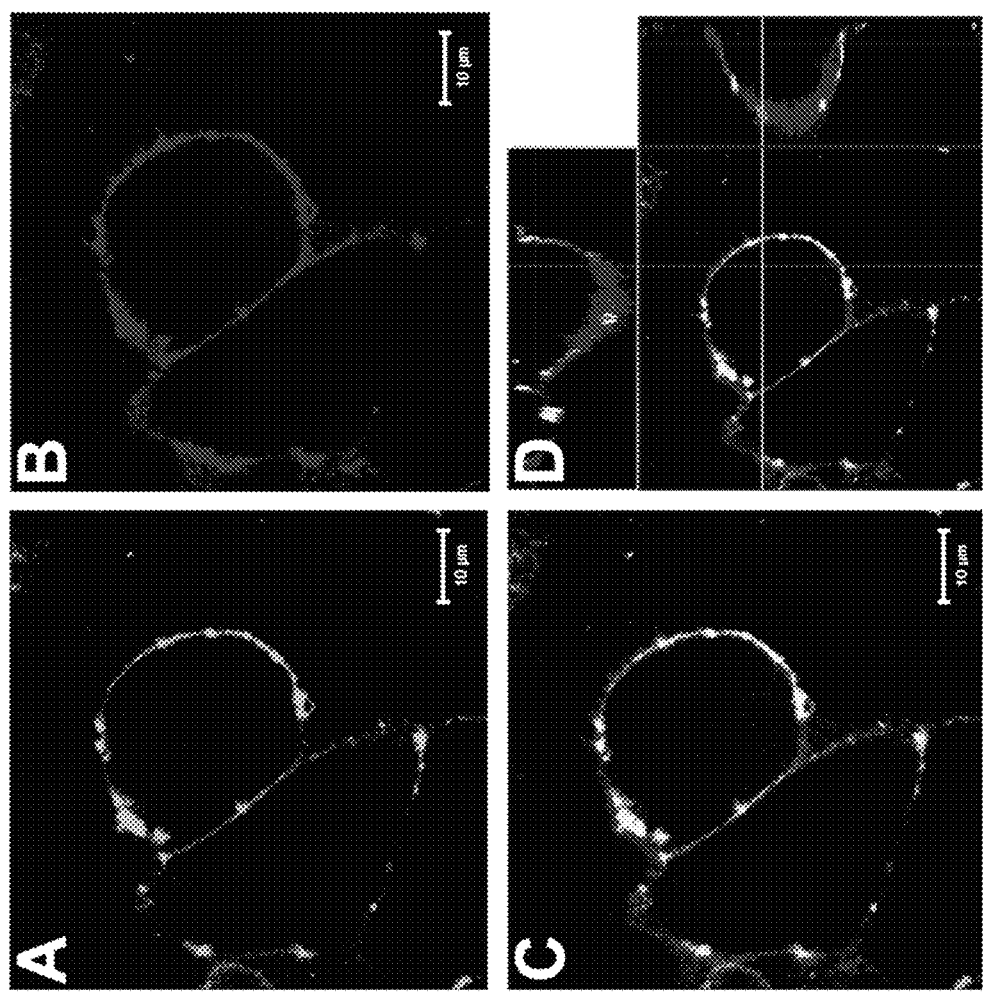
FIG. 6 displays the CLSM images of living MCF-7 cells that were incubated with 50 µM TR4 for 30 min and 10 µM DiI in PBS solution for 10 min at 37° C.; in Panel A the CLSM image of TR4 ($\lambda_{ex}$=405 nm); in panel B the CLSM image of DiI ($\lambda_{ex}$=543 nm); in panel C the merged image of panels A and B and in panel D the 3Dluminescence image of panel C.
Figure 7:
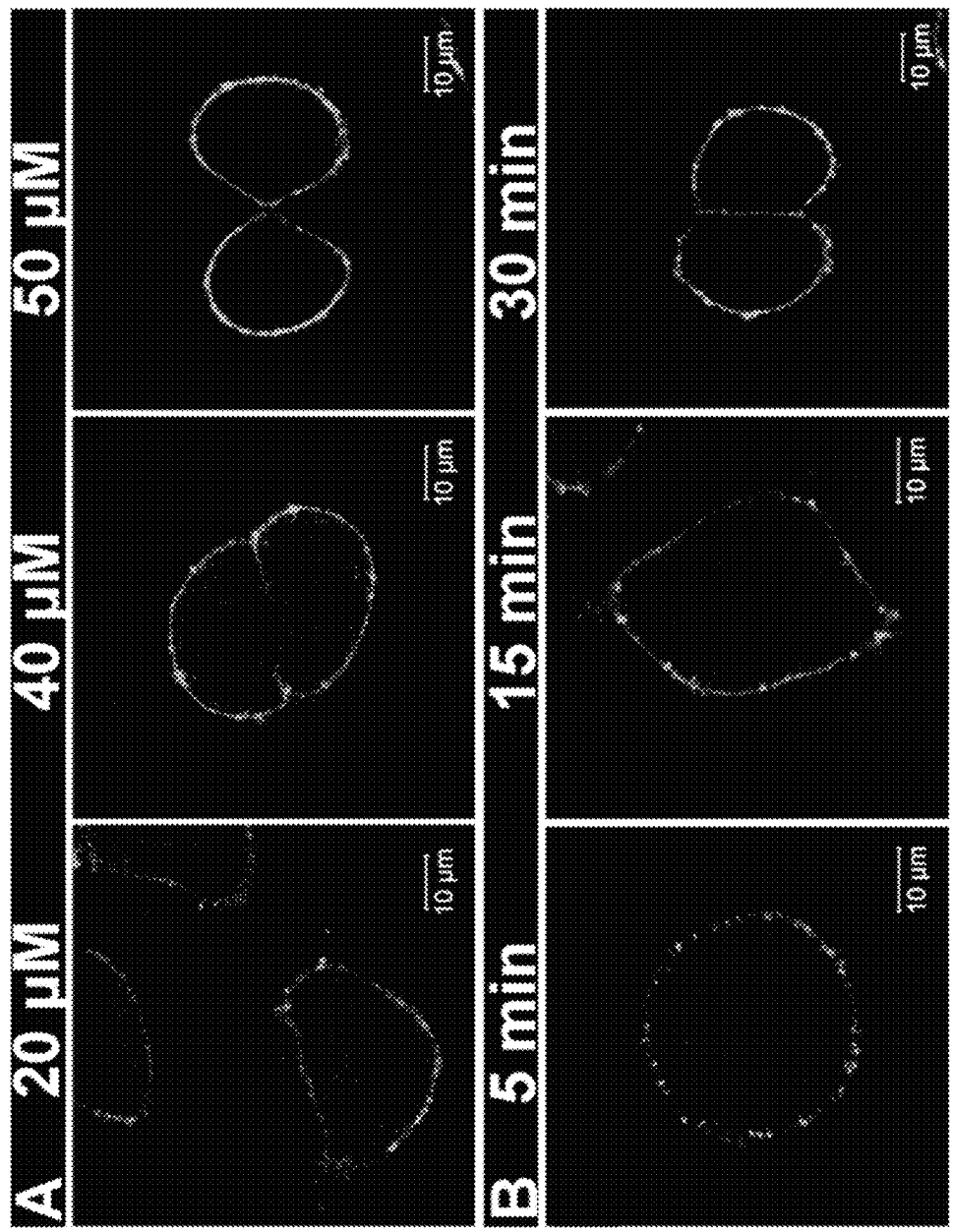
FIG. 7 displays in panel A the CLSM images of living MCF-7 cells incubated with TR4 at concentrations of 20, 40, and 50 µM for 30 min ($\lambda_{ex}$=405 nm); and in panel B the CLSM images of living MCF-7 cells incubated with TR4 at 50 µM ($\lambda_{ex}$=405 nm) for 5, 15, and 30 min.

In reference to FIG. 2, an example simple and low cost synthesis method is provided. The peptide moiety 20 was prepared by standard Fmoc solid-phase peptide synthesis (SPPS) method using CLEAR® Amide Resin and the corresponding N-Fmoc-protected amino acids with side chains properly protected. 20% piperidine in anhydrous N, N'-dimethylformamide (DMF) was used during the deprotection of the Fmoc group, then the next Fmoc-protected amino acid was coupled to the free amino group using O-(7-azabenzotriazole-1-yl)-1,1,3,3-tetramethyluronilumhexafluorophosphate (HATU) as the coupling reagent. N-Fmoc-protected and Mtt-protectd lysine was linked to the peptide 20 to form peptide moiety 22.

To couple palmitic acid (PA) to peptide 22 (Fmoc-Lys(Mtt)-Arg-Arg-Arg-Arg-$NH_2$), 3% trifluoroacetic acid (TFA) in dichloromethane (DCM) was used during the deprotection of the Mtt group and then PA was coupled to the free amino group of Lys using HATU as the coupling reagent, generating intermediate molecule 24.

In the last coupling step, carboxylated tetraphenylethylene(TPE-COOH) was used to cap the side chain amine group of the Lys in the peptide 24 (Fmoc-Lys(PA)-Arg-Arg-Arg-Arg-$NH_2$). After the last coupling step, excess reagents were removed by washing five times using DMF, followed by washing five times using dichloromethane (DCM). The peptide derivatives were cleaved from the resin by reagent containing TFA, 1,2-ethanedithiol, thioanisole and anisole and the mixture was stirred at room temperature, filtered and distilled under reduced pressure. The resulting precipitate was dissolved in acetonitrile for HPLC purification. The purified products 26 were characterized by MALDI-TOF-MS and HPLC.

In reference to FIG. 3A, a mechanism of TR4 binding to plasmid DNA is illustrated. With the four positively charged arginine tetra-peptide in TR4 molecule, it binds to negatively charged plasmid DNA 30 to form a TR4/pDNA complex 33. The formation of complex 33 can be visualized with excitation light 32 which produces a fluorescent TR4/pDNA complex 35. Thus TR4 can be used for real time monitoring DNA transfection as part of transfection reagent.

In reference to FIG. 3B, a mechanism of TR4 binding to cell membrane is illustrated. With the hydrophobic alkyl chain of PA, TR4 can stably and specifically insert into cell membrane 37, efficiently embedding TPE moiety into the lipid bilayer, producing a fluorescent cell membrane 39 under excitation light for imaging and real time tracking.

In reference to FIG. 4A, the aggregation induced emission of TR4 is measured in DMF solvent and water. Panels A and B show that in the benign solvent (DMF), TR4 (500 μM) showed no fluorescence. However, when $H_2O$ was added into the DMF solution so that the fraction was above 90% (volume %), the fluorescence intensity of TR4 (500 μM) increased dramatically (FIG. 2A, B), indicating that the fluorescence was turned on by AIE.

Panels C and D show the effect of concentration. When TR4 was added to water at low concentrations (<200 μM), it dissolved completely and existed as monodispersed molecules because of the presence of the hydrophilic moiety formed by the four arginine residues. At concentrations of 200 μM and above, the TR4 solution turned fluorescent, indicative of aggregate formation.

Panels E, F and G in FIG. 4B show the morphology change of TR4 at different concentrations by transmission electron microscopy (TEM). In panel E, no typical nanostructures were observed when the concentration of TR4 was 100 μM. In panel F, consistent with the fluorescence measurements, TR4 self-assembled into short nanofibers when the concentration was raised to 200 μM. At 500 μM, TR4 formed a greater number of longer nanofibers in panel G. These results were consistent with the fluorescence of TR4 in aqueous solution, i.e. the bright fluorescence was induced by the self-assembly of TR4 via AIE mechanism. Thus the preferred TR4 working concentration is below 100 μM in order to keep the probe in its monodispersed state and to minimize background fluorescence.

In reference to FIG. 5, TR4 binding to lipid membranes to generate fluorescent lipid membranes is shown. TR4-free liposomes with a diameter of about 100 nm were prepared by mixing hydrogenated phosphatidylcholine (hsPC) and cholesterol. The cholesterol was used to stabilize the liposomes. TR4-loaded liposomes (TR4@liposomes) were then fabricated by incubating TR4(10-100 μM) with the liposomes for 30 min. As shown in panels A and B, the emission from the TR4@liposomes was enhanced as the concentration of TR4 increased. Typically, the emission of TR4 (50 μM) in water remained weak; however, the turned-on fluorescence of TR4@liposomes (50 μM) was observed under a 365 nm lamp and verified by fluorescence spectroscopy (panel C). The integrity of TR4@liposomes was investigated by TEM. As shown in panel D, the morphology of TR4@liposomes was not changed, indicating that the insertion of TR4 did not disturb the structure of the liposomes, even though the fluorescence intensity of TR4 was markedly strengthened. The reason is probably because that after insertion of TR4 into the liposomes, the alkyl chains of the lipid bilayer restricted the rotation of the peripheral phenyl rings of TPE.

In reference to FIG. 6, TR4 is further tested with live cells. TR4 (50 μM) was incubated with MCF-7 cells to investigate its properties as a cell membrane tracker. When viewed by confocal laser scanning microscopy (CLSM), untreated MCF-7 cells showed negligible background fluorescence. However, after incubating live MCF-7 cells with TR4, bright fluorescence was observed around the cell membrane (green color; panel A). No fluorescent signal was visible in the nucleus and cytoplasm.

To further confirm the identity of the fluorescent region of the cell, the cell membrane was specifically labeled using a commercial cell membrane tracker DiI (red color, panel B). By merging the imaged region in panel C, the green TR4 signal was found to colocalize with the red DiI signal, providing evidence that TR4 colocalizes with the cytoplasmic membrane. Furthermore, three dimensional (3D) visualization also confirmed that only the cell membrane, and not the nucleus or cytoplasm, was stained by TR4 (panel D). These results indicated that TR4 is an alternative fluorescent bioprobe that can specifically stain cell membranes.

In reference to FIG. 7, the dose and staining time for TR4 to be a membrane tracker is investigated. The use of higher tracker concentrations and longer staining times could both contribute to higher fluorescence intensity, but it also may increase the risk of the tracker penetrating through the cell membrane into the cytoplasm, which would decrease the S/N ratio. Panel A shows the result of incubating MCF-7 cells with TR4 at different concentrations (20, 40, and 50 μM) for 30 min. As the TR4 concentration increased, the FL intensity of the cell membrane also increased. When MCF-7 cells were incubated with TR4 at a concentration of 20 μM, the distribution of fluorescence in the cytoplasmic membrane was punctate and not continuous. When the concentration increased to 50 μM, the distribution of fluorescence in the cytoplasmic membrane was uniform and continuous. However, interestingly, when the concentration was increased to 70 μM, the nuclear membrane was brightly labeled by TR4 (data not shown).

In panel B, the effect of staining time by incubating MCF-7 cells with TR4 at 50 μM for different times (5, 15, and 30 min), is shown. The results were similar to the effect of dose in that the FL intensity of the cell membrane was higher and the distribution was more uniform as the labeling time increased. When the incubation time was extended to 60 min, it was observed that the nuclear membrane was also labeled by TR4. It seems that TR4 is a suitable bioprobe for tracking the cell membrane and the nuclear membrane together. However, to track the cytoplasmic membrane alone, MCF-7 cells should be incubated with TR4 for 30 min at concentrations under 50 μM.

TR4 was also incubated with HepG-2 and HUVEC cells at 50 μM for 30 min and similar fluorescent staining of cytoplasmic membranes of these cells was also observed (data not shown). Subsequently, the cyto-toxicity of TR4 (0.05-50 μM) toward the MCF-7 cell line was determined by MTT assay and the cellular viability was calculated to be more that 80% in the presence of TR4 (0.05-50 μM) after incubation for 30 min (data not shown) This result indicated that TR4 has very low cyto-toxicity at the concentrations used for cell staining.

Figure 8:
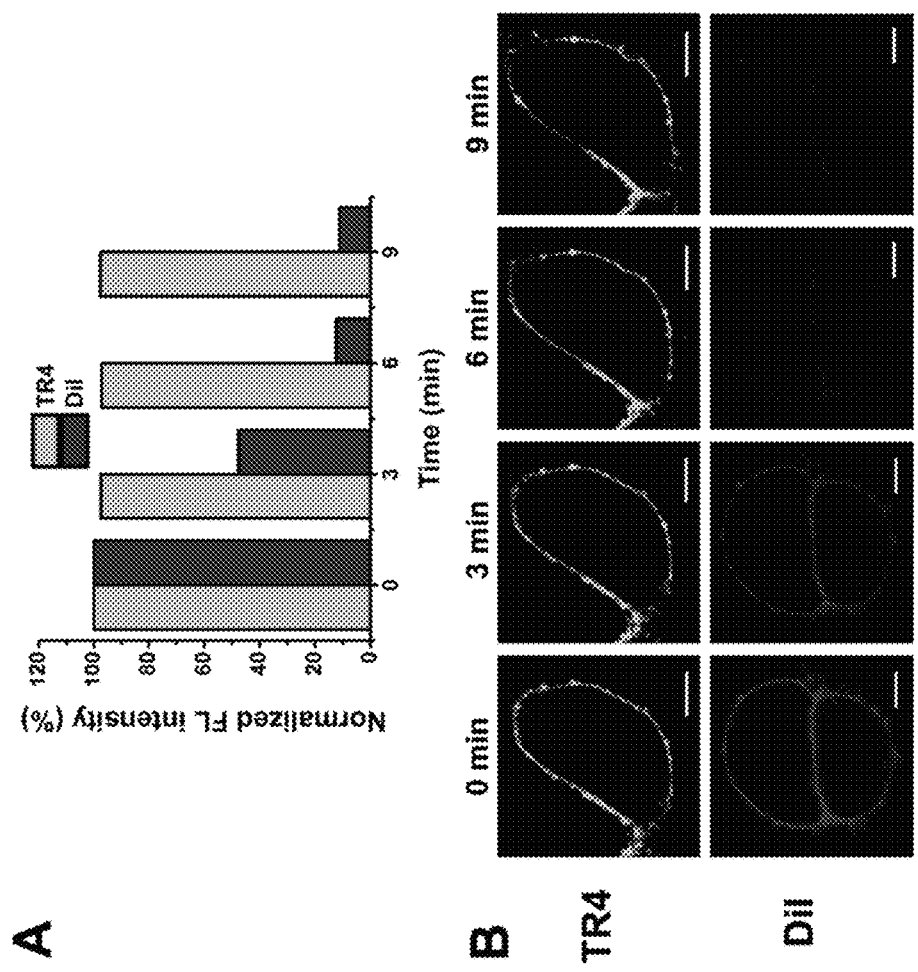
FIG. 8 displays in panel A the fluorescence intensity of living MCF-7 cells that were treated with TR4 (lighter shade) and DiI (darker shade), then scanned by CLSM for increasing amounts of time (0-9 min); in panel B the CLSM images of living MCF-7 cells treated with TR4 (upper lane) or DiI (lower lane) with increasing scanning time (0-9 min).

In reference to FIG. 8, the photostability of TR4 and DiI in living cells was investigated by continuous laser exposure using CLSM. After scanning for 9 min, the normalized fluorescence intensity from TR4 remains to be more than 95% of the starting intensity, while the normalized fluorescence intensity from DiI was only about 10% of the starting intensity (panel A). The CLSM images showed a clear dynamic difference in the fluorescence intensity of TR4 and DiI, and indicting that TR4 has superior photostability to DiI for bio-imaging.

Two-photon microscopy, which employs two near infrared photos as the excitation source has shown its advantages for deeper tissue penetration, efficient light detection and reduced photo-toxicity. Using 700 nm two-photon microscopy excitation in scanning lambda mode, the cytoplasmic membranes of TR4-labeled HUVEC cells exhibited intense fluorescence (green color) (data not shown). This gives TR4 a further advantage over traditional cell membrane dyes.

Figure 9:
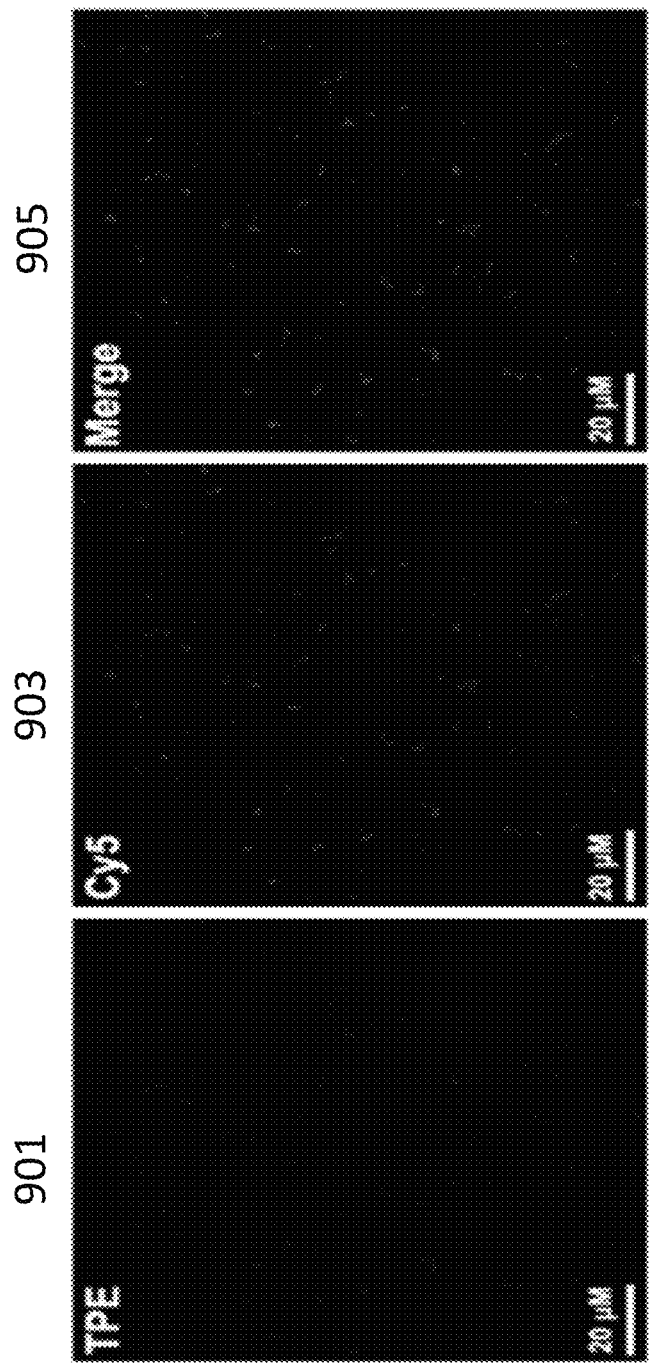
FIG. 9 displays the confocal microscopy images of TR4@Cy5-pDNA. The transfection reagent and Cy5 labeled plasmid DNA were mixed and observed under confocal microscopy.

In reference to FIG. 9, the fluorescent effect in DNA binding of TR4 is investigated. TR4 and Cy5 labeled plasmid DNA were mixed, and observed under confocal microscopy. 901 shows the image of blue fluorescence of TR4 dots (not bright in black and white figure) and 903 shows the image of red fluorescence of DNA dots. The fluorescence from transfection reagent (TR4) and the fluorescence from the DNA (Cy5) were colocalized in the merged image 905, indicating the formation of the TR4-DNA fluorescent complex.

Figure 10:
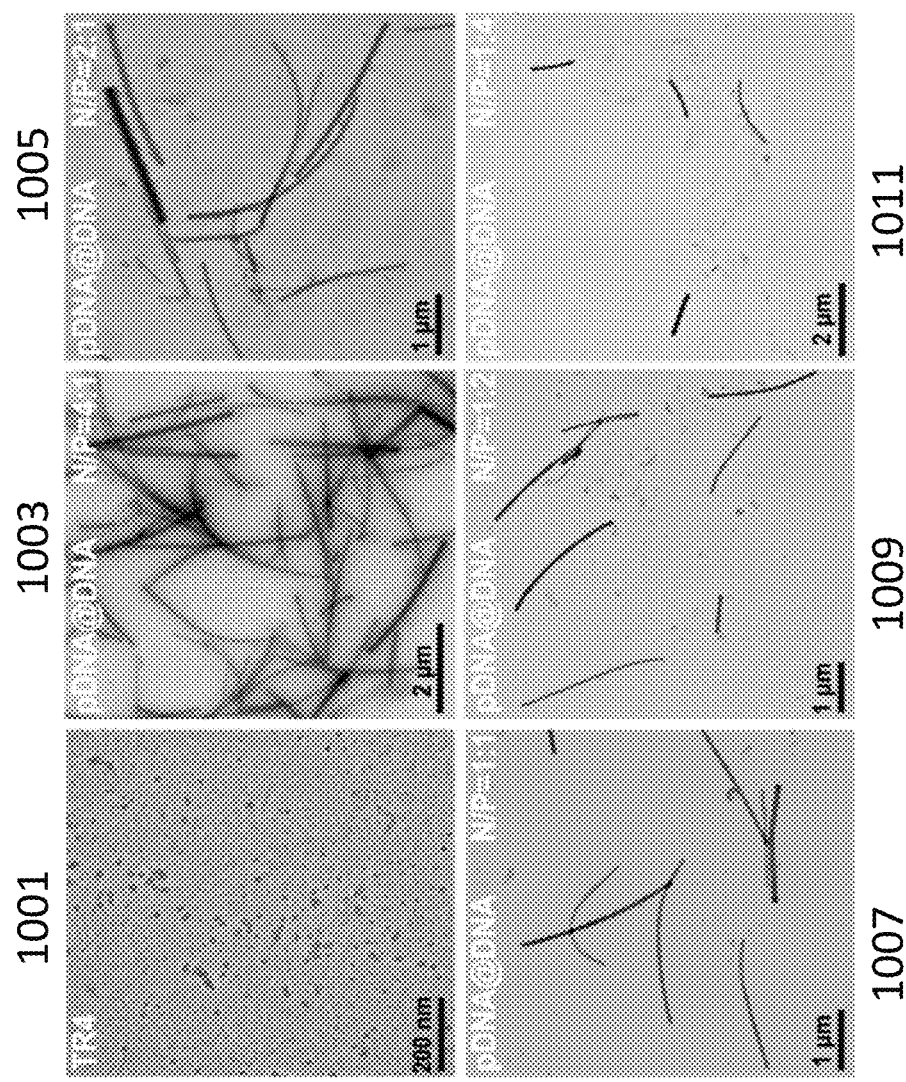
FIG. 10 displays the TEM images of pDNA/TR4 complexes with different N/P ratios. N/P is the molar ratio of the positive charges in TR4 via the phosphate groups in DNA, calculated at about 3 nmol phosphate groups in 1 µg DNA.

In reference to FIG. 10, the formation of TR4-pDNA aggregated fiber is observed under TEM. Image 1001 shows no fiber formation with TR4 alone, while image 1003 shows significant fiber formation when TR4 and pDNA are mixed at an N/P charge ratio=4:1. The formation of fiber decreases as the N/P charge ratio decreases to 2:1, 1:1, 1:2, and 1:4 in images 1005, 1007, 1009 and 1011 respectively. N/P is the molar ratio of the positive charges in TR4 verses the phosphate group charge in DNA, about 3 nmol phosphate groups in 1 μg DNA.

Figure 11:
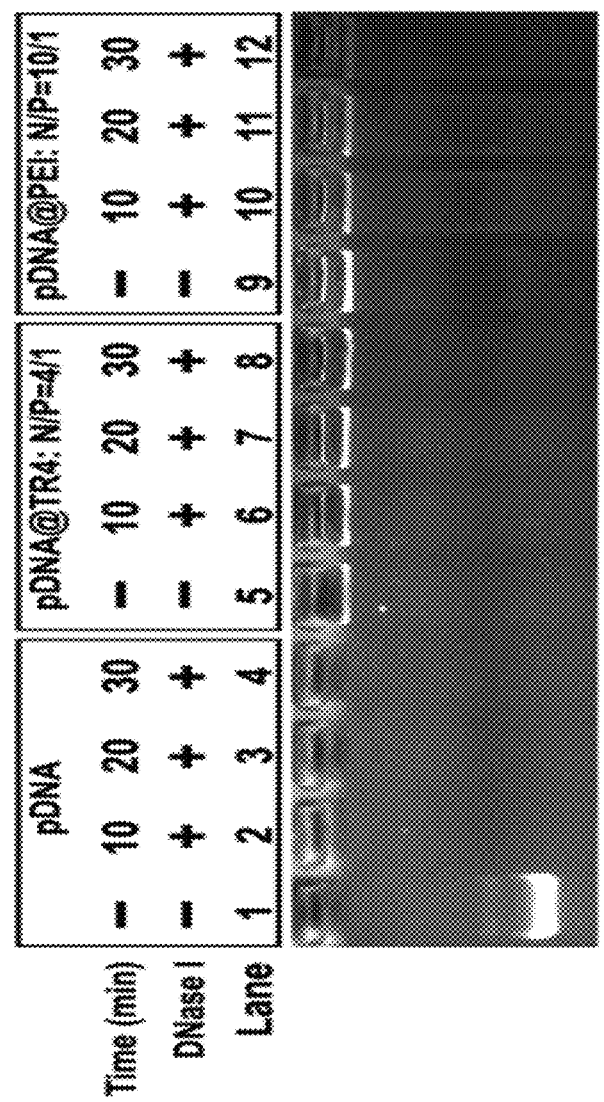
FIG. 11 shows the pDNA/TR4 complex's resistance to nuclease treatment as shown by agarose gel electrophoresis.

In reference to FIG. 11, TR4@pDNA complex formation by its capacity resist to nuclease digestion. Agarose gel eletrophorisis is shown. Lanes 1-4 show the digestion of plasmid DNA by DNase I treatment. Lanes 5-8 show that the TR4@pDNA complex at N/P=4:1 is fully resistant to DNase I treatment while Lanes 9-12 show that the PEI-pDNA complex at N/P=10:1 is less resistant to 30 min DNase I treatment.

Transfection description: Preparing TR4@DNA complex: First, dissolve TR4 powder in pure water to make 1 mM TR4 stock solution. Then 82.8 μL TR4 stock solutions was mixed with 24.0 μg EGFP-N1 plasmid DNA, storing in the room temperature for 10 min to form the complex. Next, the complex was diluted into 1.2 mL 5% dextrose solutions as TR4@DNA stock solution for transfection. In addition, the fluorescence of this stock solution became observable upon mixing TR4 with DNA, indicating the formation of the TR4@pDNA complexes. Cell culture and transfection: The cells were seeded in 12-well plates at $8 \times 10^4$ cells per well and cultured in 1 mL H-DMEM supplemented with 10% FBS, 100 U/mL penicillin and 100 mg/mL streptomycin for 24 hours. Before the transfection, the cells were starved for 15 min using Opti-MEM. Then, the medium was replaced by the TR4@DNA stock solution diluted by 1 mL Opti-MEM containing 2 μg pDNA in each well. After being cultured for 4 hours, the medium was exchanged with supplemented H-DMEM for another 44 hours. The expression of EGFP-N1 plasmid was directly observed by fluorescence microscope and the transfection efficiency was determined by cytometer.

Figure 12:
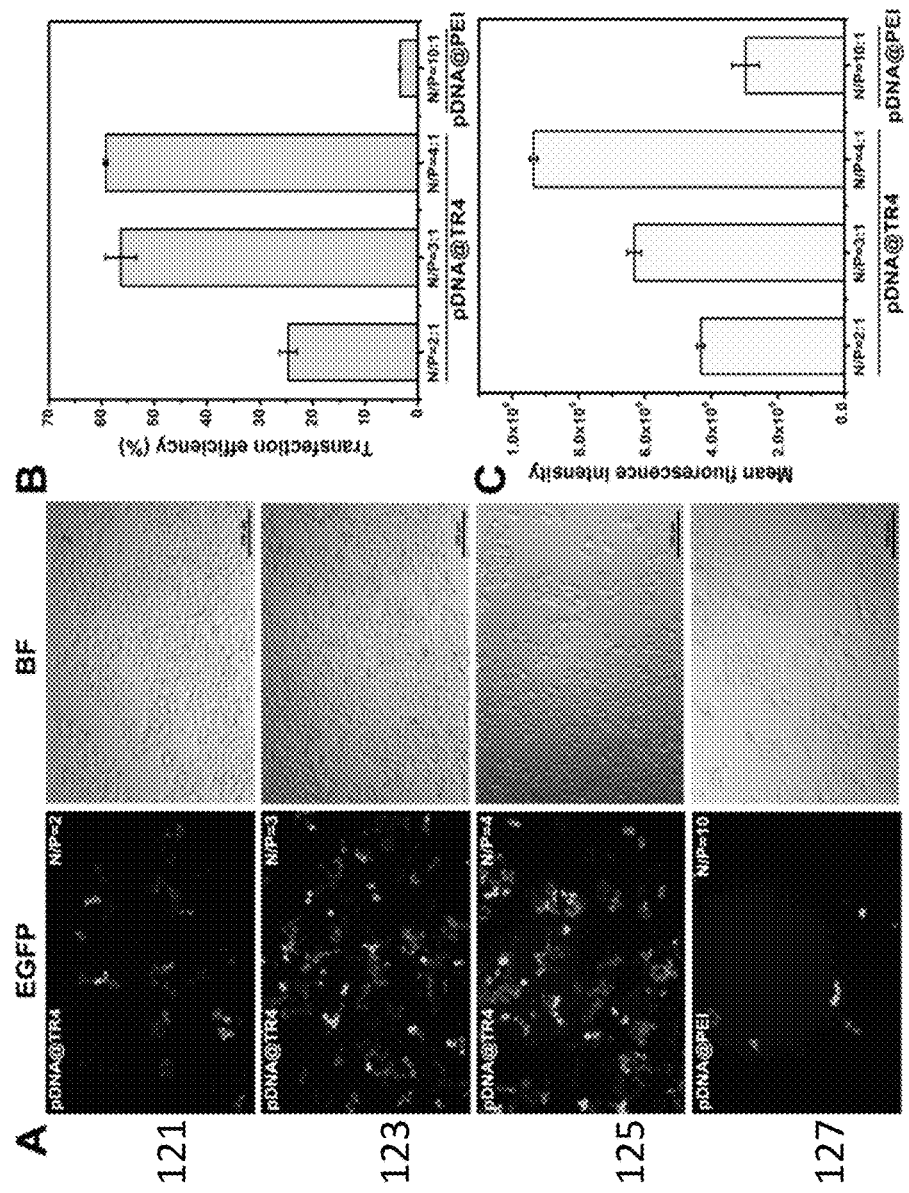
FIG. 12 shows the efficiency of gene transfection with pDNA/TR4 complexes in Hela cells in comparison to pDNA/PEI complexes.

In reference to FIG. 12, gene transfection efficiency of TR4@pDNA complexes in Hela cells is compared to that of pDNA@PEI complexes. Plasmid DNA containing EGFP gene is transfected and the fluorescence of the expressed EGFP is measured as the indicator for gene transfection efficiency. In panel A, confocal microscope images 121, 123, 125 show the EGFP expression (left side) in Hela cells transfected with the aid of TR4, while on the right side show the corresponding blue fluorescence from TR4@pDNA complexes. Confocal microscope images 127 shows the EGFP expression (left side) in Hela cells transfected with the aid of PEI while on the right side show the corresponding blue fluorescence from pDNA@PEI complexes. Panel B shows the transfection efficiency of the corresponding various pDNA@TR4 complexes, where the transfection efficiency of EGFP expression plasmid@TR4 complexes can reach as high as 60% in Hela cells while EGFP expression plasmid/PEI remains less than 5%. Panel C shows the fluorescence produced from TR4@pDNA complexes correlates to the transfection efficiency.

Figure 13:
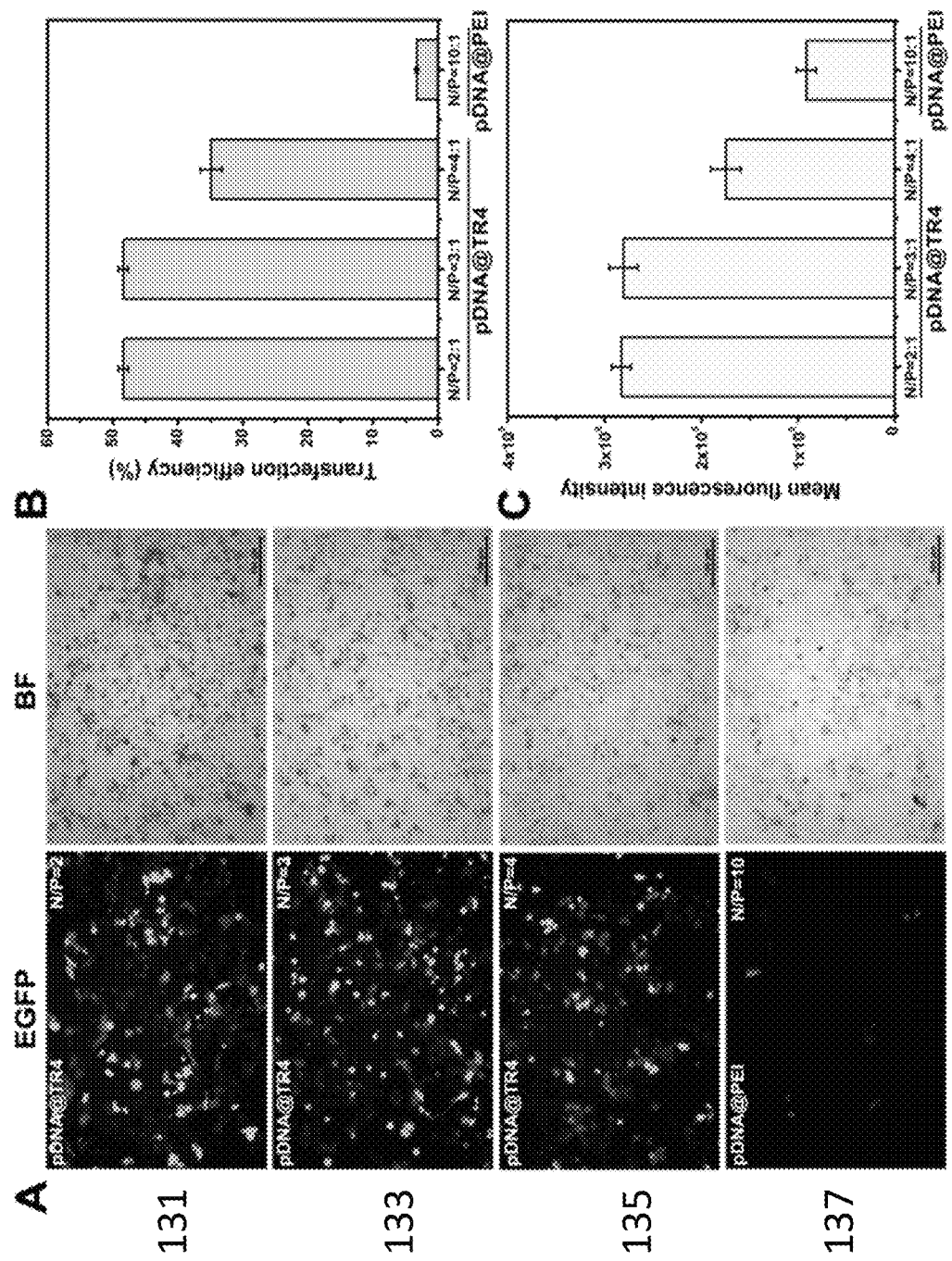
FIG. 13 shows the efficiency of gene transfection with pDNA/TR4 complexes in HepG2 cells in comparison to pDNA/PEI complexes.

In reference to FIG. 13, gene transfection efficiency of TR4@pDNA complexes in HepG2 cells (more difficult to transfect) is compared to that of TR4@pDNA complexes. Plasmid DNA containing EGFP gene is transfected and the fluorescence of the expressed EGFP is measured as the indicator for gene transfection efficiency. In panel A, confocal microscope images 131, 133, 135 show the EGFP expression (left side) in HepG2 cells transfected with the aid of TR4, while on the right side show the corresponding blue fluorescence from TR4@pDNA complexes. Confocal microscope images 137 shows the EGFP expression (left side) in HepG2 cells transfected with the aid of PEI while on the right side show the corresponding blue fluorescence from TR4@pDNA complexes. Panel B shows the transfection efficiency of the corresponding various TR4@pDNA complexes, where the transfection efficiency of EGFP expression plasmid@TR4 complexes can reach as high as 50% in HepG2 cells while EGFP expression plasmid@PEI remains less than 5%. Panel C shows the fluorescence produced from TR4@pDNA complexes correlates to the transfection efficiency.

Figure 14:
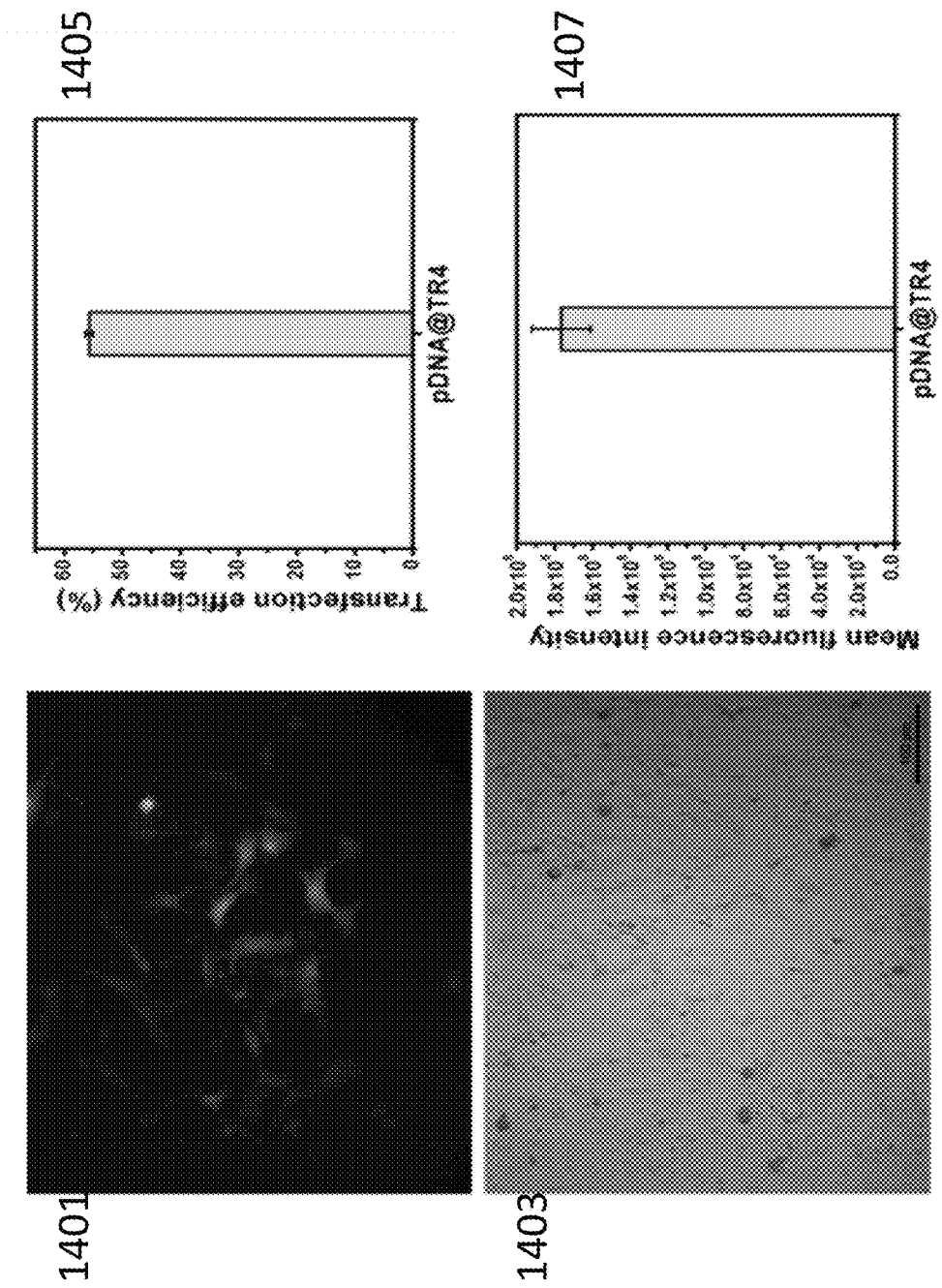
FIG. 14 shows the efficiency of gene transfection of pDNA/TR4 complexes in NIH 3T3 cells.

In TR4@pDNA reference to FIG. 14, gene transfection efficiency of TR4@pDNA complexes in NIH 3T3 cells is compared to that of pDNA@PEI complexes. NIH 3T3 cells are commonly known in the field for being difficult to transfect with non-virus gene carriers. Plasmid DNA containing EGFP gene is transfected and the fluorescence of the expressed EGFP is measured as the indicator for gene transfection efficiency. Confocal microscope image 1401 shows the EGFP expression in NIH 3T3 cells transfected with the aid of TR4, while confocal microscope image 1403 shows the corresponding blue fluorescence from TR4@pDNA complexes. There was no or negligible expression of EGFP in NIH 3T3 cells transfected with TR4@pDNA complexes. Graph 1405 shows the transfection efficiency of EGFP expression plasmid/TR4 complexes can still reach as high as more than 50%. Graph 1407 shows that the fluorescence produced from TR4@pDNA complexes correlates to the transfection efficiency.

Figure 15:
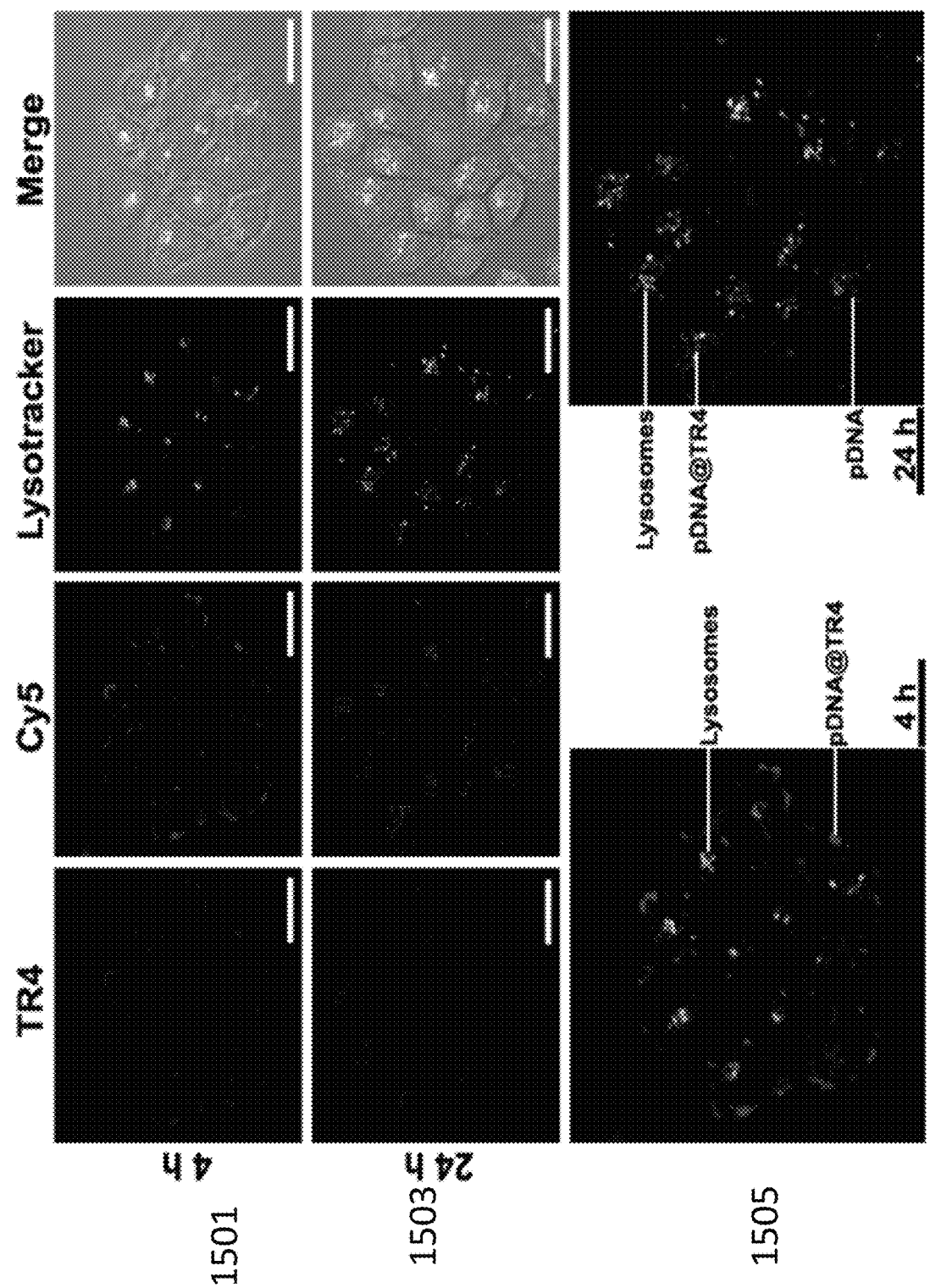
FIG. 15 displays the confocal microscopy images of HeLa cells transfected with TR4@pDNA complexes at 4 hour or 24 hour after transfection.

In reference to FIG. 15, the intracellular distribution of TR4@pDNA complexes in HeLa cells is monitored with DNA specific dye Cy5 and a lysosome tracking dye. Under confocal microscope, TR4@pDNA complex emits blue lights, Cy5-DNA emits red color, lysotracker that stains lysosomes emits bright green color. Image lane 1501 shows the images taken after 4 hours of TR4@pDNA transfection, image lane 1503 shows the images taken after 24 hours of TR4@pDNA transfection. Image lane 1505 displays enlarged merged images of one cell at 4 hour of transfection and 24 hour of transfection respectively, showing that blue color and red color dots are co-localizing while green color dots are not co-localizing with red color and blue color dots. At 4 hr of transfection, most of the TR4@pDNA complexes are attached at the cell surface, at 24 hr of transfection, most of the TR4@pDNA complexes entered into cells and some of plasmid DNA were released from the TR4@pDNA complex, became free plasmid DNA. TR4@pDNA complexes entered cells not through endocytosis and effectively escaped from endosomes. The effective escape from lysosome digestion may contribute to the observed high transfection efficiency in all tested cell types.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A fluorescence molecular agent, comprising a compound represented by a chemical formula:

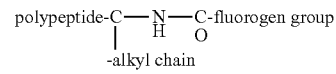

wherein said fluorogen group exhibits aggregation-induced emission, and said alkyl chain contains at least a 8-20 carbon length alkyl group.

2. The fluorescence molecular agent in claim 1, wherein said polypeptide in the chemical formula comprises a sequence of 4 to 20 positively charged amino acids.

3. The fluorescence molecular agent in claim 1, wherein the C carbon in the chemical formula is the α carbon of a lysine residue, said alkyl chain is linked to the R side chain of the lysine residue, and the NHCO amide bond is formed by the α-amine of the lysine residue.

4. The fluorescence molecular agent in claim 3, wherein the polypeptide is a tetra-peptide sequence consisting of four arginine residues, the fluorogen group is tetraphenylethylene or tetraphenylsilole, and the alkyl chain is from a palmitic acid, oleic acid or stearic acid.

5. The fluorescence molecular agent in claim 3, wherein said poly-peptide and said lysine residue is first synthesized through a solid-phase peptide synthesis process, a carboxylated hydrophobic alkyl chain is then conjugated to the amino group of the side chain of the lysine residue and a carboxylated AIE fluorogen group is lastly conjugated to the α-amine of the lysine residue to form the NHCO amide bond using HATU (1-[Bis(dimethylamino)methylene]-1H-1,2,3-triazolo[4,5-b]pyridinium 3-oxid hexafluorophosphate) and DIEA (N, N-Diisopropylethylamine) as catalysts.

6. The fluorescence molecular agent in claim 4, wherein said fluorescence molecular agent is placed into a cell culture medium with live cells at a concentration ranging from 10-50 μm.

7. The fluorescence molecular agent in claim 4, wherein the fluorescence molecular agent binds unto or into a bilayered lipid membrane or a cell cytomembrane to generate a fluorescent bilayered lipid membrane or a fluorescent cell cytomembrane.

8. The fluorescence molecular agent in claim 4, wherein the fluorescence molecular agent binds with a plasmid DNA or a DNA fragment to generate a fluorescent DNA complex.

9. The fluorescence molecular agent in claim 4, wherein the fluorescence molecular agent is in a cell transfection solution, allowing to observe a cell transfection process live.

10. A DNA cell transfection method, comprising the steps of:
    mixing a solution of the fluorescence molecular agent of claim 4 with a transfection DNA solution to form a DNA transfection complex solution;
    adding said DNA transfection complex solution to a live cell culture; and
    observing said DNA transfection complex having fluorescent color under a confocal microscope.

* * * * *